United States Patent
Xie et al.

(10) Patent No.: US 7,692,056 B2
(45) Date of Patent: *Apr. 6, 2010

(54) PROCESS FOR PRODUCING LOWER OLEFINS FROM METHANOL OR DIMETHYLETHER

(75) Inventors: Zaiku Xie, Shanghai (CN); Juntao Liu, Shanghai (CN); Weimin Yang, Shanghai (CN); Siqing Zhong, Shanghai (CN); Xiaofeng Chen, Shanghai (CN)

(73) Assignee: Shanghai Research Institute of Petrochemical Technology Sinopec, Shanghai (CN)

( * ) Notice: Subject to any disclaimer, the term of this patent is extended or adjusted under 35 U.S.C. 154(b) by 244 days.

This patent is subject to a terminal disclaimer.

(21) Appl. No.: 11/503,913

(22) Filed: Aug. 15, 2006

(65) Prior Publication Data

US 2007/0038011 A1    Feb. 15, 2007

(30) Foreign Application Priority Data

Aug. 15, 2005    (CN) ..................... 2005 1 0028809

(51) Int. Cl.
    *V07C 1/00*    (2006.01)
(52) U.S. Cl. ...................... 585/640; 585/639
(58) Field of Classification Search ......... 585/651–653, 585/639, 640, 312, 324
    See application file for complete search history.

(56) References Cited

U.S. PATENT DOCUMENTS 4,404,414 A * 9/1983 Penick et al. ............... 585/469
5,367,100 A * 11/1994 Gongwei et al. ............ 585/640
6,797,851 B2 * 9/2004 Martens et al. ............. 585/640
7,015,369 B2 * 3/2006 Hack et al. .................. 585/640
2004/0024276 A1 * 2/2004 Smith et al. ................. 585/639

* cited by examiner

*Primary Examiner*—In Suk Bullock
(74) *Attorney, Agent, or Firm*—Birch, Stewart, Kolasch & Birch, LLP.

(57) ABSTRACT

The present invention provides a process for producing lower olefins from methanol or dimethyl ether. The technical problem mainly addressed in the present invention is to overcome the defects presented in the prior art including high operation temperature, low yield and selectivity of lower olefins as the target products, and poor stability and short regeneration period of catalyst. The present process, which is carried out under the conditions of catalytic cracking methanol and dimethyl ether and the presence of diluting gas, and adopts as a feedstock methanol, dimethyl ether or their mixture, comprises the steps of: a) letting the feedstock firstly enter a first reaction zone to contact with a first crystalline aluminosilicate catalyst having a $SiO_2/Al_2O_3$ molar ratio of at least 10, to thereby produce a first reaction effluent containing lower olefins; b) letting the first reaction effluent enter in turn at least one second reaction zone to contact with a second crystalline aluminosilicate catalyst having a $SiO_2/Al_2O_3$ molar ratio of at least 10, to thereby produce a second reaction effluent containing lower olefins; and c) separating lower olefins from the second reaction effluent; wherein the weight ratio of the diluting gas to the feedstock is 0.01-6:1, while controlling the reaction conditions.

13 Claims, No Drawings

PROCESS FOR PRODUCING LOWER OLEFINS FROM METHANOL OR DIMETHYLETHER

CROSS REFERENCE

The present application claims the priority of the patent application with Ser. No. 200510028809.6 as filed with the State Intellectual Property Office of China on Aug. 15, 2005, which is incorporated herein for reference in its entirety for all purposes.

TECHNICAL FIELD

The present invention relates to a process for producing lower olefins from methanol or dimethyl ether, and in particular to a process for producing lower olefins by virtue of catalytic cracking of methanol or dimethyl ether.

BACKGROUND ART

Petrochemical industry is an important supporting industry in national economy, and supplies a large quantity of chemical raw materials for various departments including industry, agriculture, communication and national defense, which is thus one of the industrial sectors taking correlative and leading action in national economy. Lower olefins are one of the most important basic raw materials constituting modern petrochemical industry.

For instance, propylene is mainly used for the production of polypropylene, cumene, oxo alcohol, acrylonitrile, propylene oxide, acrylic acid, isopropanol and etc., wherein polypropylene accounts for more than half of the demand for propylene in the world. At present, 67% of propylene in the world is derived from by-products in the production of ethylene by steam cracking, 30% of which is derived from by-products in the production of gasoline and diesel oil by catalytic cracking unit (FCC) in refinery, and low amount of which (about 3%) is obtained from dehydrogenation of propane and metathesis reaction of ethylene-butylene. It is predicted that the demand of propylene in the future will be increased in a higher rate than the supply thereof.

Considering the relatively higher rate of increase in term of demand of propylene, and the situation of "demand exceeds supply" presented in conventional production modes, it is necessary to recur to other various new techniques of increasing yield of propylene for the purpose of supplementing the demand of propylene.

For many years, much experience has been achieved in the techniques of preparation of syngas from coal or natural gas, the preparation of methanol from syngas and separation of olefins for large-scale productions. Nevertheless, the process from methanol to olefins is still an unsolved and difficulty problem for the above industrial production chain from syngas to olefins. Solving the above key technique could provide a new resource approach for an industrial production of basic chemical materials, ethylene and propylene, from non-petroleum resources. In Particular, the demand for ethylene and propylene is continuingly increasing in recent years, while the petroleum resources are gradually exhausted. A development of a new coal-based chemical approach for the industrial production of lower olefins is of important strategic meaning and socioeconomic value in our country in greatly alleviating the situation of short petroleum supply, promoting a rapid progress of heavy chemical industry and constructive adjustment of resources.

The reference document CN1166478A disclosed a process for production of lower olefins such as ethylene and propylene from methanol or dimethyl ether. The process used an aluminophosphate molecular sieve as catalyst, and was an up-flowing dense phase circular fluidized process. Under the preferred reaction temperature of 500-570□, WHSV of 2-6 $hr^{-1}$ and pressure of 0.01-0.05 MPa, methanol or dimethyl ether is cracked to produce lower olefins such as ethylene and propylene. The process, on the one hand, required a higher temperature, and on the other hand produced the target products with low selectivity. In addition, the fluidized bed technique has a technical defect of requiring relatively higher investment and operation costs.

The reference document CN1356299A disclosed a process and its system for production of lower olefins from methanol or dimethyl ether. The process used aluminophosphate molecular sieve (SAPO-34) as catalyst, and a gas-solid parallel down-flowing fluidized bed reactor for super-short contact, where the catalyst and the feedstock contacted with each other and the reactant stream was down-flowing. The obtained products and the catalyst flowed out of the reactor and then entered into the gas-solid rapid separator at the lower portion of the reactor for a rapid gas-solid separation. The separated catalyst entered into a regenerator to burn off the coke produced for regeneration. The catalyst was continuously regenerated in the system and the reaction was carried our continuously. The conversion of methanol was greater than 98% in the process. Nevertheless, the process equally presented a technical defect of requiring relatively higher investment and operation costs, and of lower selectivity to lower olefins.

CONTENTS OF THE INVENTION

The technical problem to be solved in the present invention is to overcome the defects presented in the prior documents including high operation temperature, low yield and selectivity of lower olefins as the target products, and poor stability and short life of catalyst, and the present invention put forward a novel process for producing lower olefins from methanol and dimethyl ether. After making extensive and intensive analysis on the complicated mechanism of catalytic cracking reaction of olefins, the present inventors have made a lot of experimental researches and explorations, closely combining macroscopic exhibition and microscopic essence of the experimental phenomena, in light of basic principles of heat transfer, thereby put forward a novel technical solution for solving those problems.

The present process is featured with high yield and good selectivity in term of lower olefins as the target product, as well as high stability and long life of the catalyst.

The process for producing lower olefins herein, which is carried out under the conditions of catalytic cracking methanol and dimethyl ether and the presence of diluting gas, and adopts as a feedstock methanol, dimethyl ether or their mixture, comprises the steps of:

a) letting the feedstock firstly enter a first reaction zone to contact with a first crystalline aluminosilicate catalyst having a $SiO_2/Al_2O_3$ molar ratio of at least 10, to thereby produce a first reaction effluent containing lower olefins;

b) letting the first reaction effluent enter in turn at least one second reaction zone to contact with a second crystalline aluminosilicate catalyst having a $SiO_2/Al_2O_3$ molar ratio of at least 10, to thereby produce a second reaction effluent containing lower olefins; and c) separating lower olefins from the second reaction effluent;

wherein, the weight ratio of the diluting gas to the feedstock is 0.01-6:1, the reaction temperature in the first reaction zone is 190-500° C., and the reaction pressure in the first reaction zone is −0.1-1 MPa; and the reaction temperature in the second reaction zone is 400-580° C., and the reaction pressure in the second reaction zone is −0.09-0.5 MPa, with the proviso that the first reaction zone has a different reaction temperature and/or pressure from the second reaction zone.

The term "lower olefins" used herein refers to olefins having 2 to 6 carbon atoms.

In the present process, the mixture of methanol and dimethyl ether could be their mixture in any ratio. The diluting gas used herein is preferably selected from water steam, ethanol vapor or their mixture in any ratio. The weight ratio of the diluting gas to the feedstock is preferably 0.2-3:1. The diluting gas is first thoroughly mixed with the feedstock, and the mixture is then subject to vaporization prior to entry into reaction zones.

The second reaction effluent herein passes in turn such as ethylene separation tower and propylene separation tower to thereby obtain lower olefins product such as ethylene and propylene. Such process of separating lower olefins is well known to a person skilled in the art.

In one embodiment of the invention, the first reaction zone has a reaction temperature of preferably 200-500° C., a weight hourly space velocity (WHSV, the weight of feedstock passed per hour per unit weight of catalyst) of preferably 0.1-70 $hr^{-1}$, and a reaction pressure (gauge pressure, the same below) of preferably −0.1-1 MPa; more preferably, the reaction temperature is 300-480° C., WHSV is 1-50 $hr^{-1}$, the reaction pressure is −0.04-0.5 MPa. The second reaction zone has a reaction temperature of preferably 400-580° C., a WHSV of preferably 0.1-50 $hr^{-1}$, and a reaction pressure of preferably −0.09-0.5 MPa; more preferably, the reaction temperature is 450-550° C., WHSV is 1-20 $hr^{-1}$, the reaction pressure is −0.04-0.5 MPa.

In another more preferred embodiment of the invention, both the first and second reaction zones have a pressure of −0.1-<0 MPa.

The first crystalline aluminosilicates used herein are preferably selected from solid acid molecular sieve catalysts, for instance, ZSM molecular sieve, Y molecular weight, beta molecular sieves or mordenite, such as ZSM-5, ZSM-11, ZSM-23 or ZSM-42 molecular sieves, having a $SiO_2/Al_2O_3$ molar ratio of 10-1000. The second crystalline aluminosilicates used herein are preferably selected from solid acid molecular sieve catalysts, for instance, ZSM molecular sieve, Y molecular weight, beta molecular sieves or mordenite, such as ZSM-5, ZSM-11, ZSM-23 or ZSM-42 molecular sieves, having a $SiO_2/Al_2O_3$ molar ratio of 80-800. Both of the first and second crystalline aluminosilicates are, more preferably, ZSM-5 molecular sieves having a $SiO_2/Al_2O_3$ molar ratio of 100-700.

In one preferred embodiment of the process of the invention, said at least one of the second reaction zones preferably includes 1-5 reactors in series, more preferably 1-3 fixed-bed reactors in series. In which, the fixed-bed reactor is preferably selected from axial fixed-bed, radial fixed-bed reactors and moving bed reactors.

In one preferred embodiment, the reaction temperature of the first reaction zone is lower than the second reaction zone, preferably by 30-150☐, and/or the WHSV is higher than the second reaction zone, preferably by 3-20 $hr^{-1}$. The invention adopts at least two reaction zones in series, wherein, in comparison, the first reaction zone is operated at a higher WHSV and a lower temperature, and the second reaction zone is operated at a lower WHSV and a higher temperature. The preparation of lower olefins from methanol or dimethyl ether is a strongly exothermic process. For a fixed-bed process, the centralized liberation of heat during the dehydration may cause a relatively greater temperature increase of the catalyst at the inlet, in particular the local temperature at active center of the catalyst may be higher by tens or even above 100 centigrade than the apparent temperature of the catalyst, and a too high local temperature increase has a very fatal influence on the life of the catalyst. In particular, it may greatly promote the process of coking and thus deactivation of the catalyst and shortening its stable period.

A lower temperature operation used in the first reaction zone may alleviate thermal discharge from dehydration of methanol or dimethyl ether, to thereby avoid, during the preparation of olefins from methanol or dimethyl ether, a too high local temperature increase that may cause rapid deactivation of the catalyst. Meanwhile, a relatively higher WHSV is used therein for the purpose of avoiding hydrogen transfer reactions of the resulted preliminary products at lower temperature that may reduce the yield and selectivity of the target products. In addition, considering the facts that the dehydration of methanol or dimethyl ether inevitably produces C4 or higher olefins, and then such olefins are able to be cracked into lower olefins at a higher temperature, and the cracking process is endothermic, a relatively higher operation temperature and a relatively lower WHSV are used in the second reaction zones connected in series, so as to guarantee sufficient conversion of methanol or dimethyl ether to improve the selectivity and yields of lower olefins, to thereby fulfill the purpose of maximizing the yield of lower olefins and prolonging the stable period of the catalyst.

The purpose of adopting the second reaction zone also resides in providing heat absorption needed in cracking reaction by the virtue of dehydration-heat liberation of the organic oxygenate compound, and at the same time providing additional diluting gas, so that the intermediate procedures and energy during the reactions are effectively utilized by an effective combination of two kinds of the reactions mentioned above.

The technical solution of the invention achieves a preferable technical effect, which effectively prolongs the stability of the catalyst activity with the proviso of lowering the reaction temperature and increasing the yield and selectivity of lower olefins as the target products (for instance, the yield of propylene herein could reach 47%).

Reference could be made to conventional catalytic cracking process of lower olefins with respect to other operation conditions that are not specifically described herein but may be involved in the present process for producing lower olefins by catalytic cracking.

Unless identified otherwise, the percentages and ratios used herein are all on the basis of weight.

Unless identified otherwise, the $SiO_2/Al_2O_3$ molar ratio of the crystalline aluminosilicates in the present invention is calculated on atomic basis.

All the publications mentioned are incorporated herein for reference in their entirety for all purposes.

The following examples further describe and demonstrate the preferred embodiments of the present inventions. All of the examples are merely illustrative, not interpreted as limiting to the present inventions.

In the examples, the amounts of various components in each of the mixtures involved are separated and detected with HP-6890 gas chromatograph (Agilent Technologies, Inc., the United States), equipped with thermal conductivity detector (TCD) and a hydrogen flame ion detector (FID) and a Φ0.53 mm PLOT Q capillary chromatographic column of length of 50 meters.

The methanol and dimethyl ether used in the following examples are of purity of chemical grade.

EXAMPLES

Example 1

Raw materials in a molar ratio of 200 $SiO_2$:0.5 $Al_2O_3$: 60 n-butyl amine: 17 $OH^-$: 200 NaCl : 6300 $H_2O$ were mixed with stirring at room temperature for 15 hr to formulate a slurry containing silicon, aluminum, template (n-butyl amine) and water in light of a $SiO_2/Al_2O_3$ molar ratio of 200. Thereafter, the slurry was crystallized at 140° C. for 50 h, followed by washing the crystallized solution with distilled water, drying it at 120° C. in an air atmosphere for 12 hr and then calcining at 580° C. in an air atmosphere for 8 hr to obtain ZSM-5 molecular sieve. 50 g of the ZSM-5 molecular weight was mixed with 87 g of 40% (weight) silica gel, and extruded to obtain strips followed by drying them at 130° C. in an air atmosphere for 12 hr and calcining at 430° C. in an air atmosphere for 6 hr to obtain a ZSM-5 type catalyst.

5 g of the above ZSM-5 type catalyst was respectively loaded into first and second reactors in series (both of which are Φ8 mm axial fixed-bed reactors, the same in the following examples). The first reactor had a reaction temperature of 210° C., a WHSV of 50 $hr^{-1}$, and a pressure of 1 MPa; and the second reactor had a reaction temperature of 420° C., a WHSV of 12 $hr^{-1}$, and a pressure of −0.068 MPa. The feedstock used in the experiment was pure methanol, and the weight ratio of water steam to methanol is 0.05. The water in the needed amount was first mixed with methanol and then the mixture was subject to vaporization prior to enter into the reactor. The product was analyzed by sampling after reacting for 2 hr. The reaction results were as follows: the yield of propylene was 30%, the yield of ethylene was 5%, and the conversion of methanol was 93%.

Example 2

The various steps and conditions in this example were the same as those in Example 1, except that: the molecular sieves in both the first and the second reactor were ZSM-5 molecular sieve catalyst having a $SiO_2/Al_2O_3$ molar ratio of 750; the first reactor had a reaction temperature of 300° C., a WHSV of 65.0 $hr^{-1}$ and a reaction pressure of 0.8 MPa; and the second reactor had a reaction temperature of 460° C., a reaction pressure of 0.42 MPa and a WHSV of 1 $hr^{-1}$. The feedstock used herein was the mixture of methanol and dimethyl ether in a weight ratio of 1:1, and the weight ratio of water steam to the total amount of methanol and dimethyl ether is 5. The water in the needed amount was first mixed with the feedstock and then the mixture was subject to vaporization prior to enter into the reactor. The product was analyzed by sampling after reacting for 2 hr. The reaction results were as follows: the yield of propylene was 35.54%, the yield of ethylene was 6.13%, and the conversion of methanol was 98.5%.

Example 3

The various steps and conditions in this example were the same as those in Example 1, except that: the molecular sieve in the first reactor was ZSM-5 molecular sieve catalyst having a $SiO_2/Al_2O_3$ molar ratio of 100, the first reactor had a reaction temperature of 480° C., a WHSV of 10.0 $hr^{-1}$ and a reaction pressure of −0.08 MPa; the molecular sieve in the second reactor was ZSM-5 molecular sieve catalyst having a $SiO_2/Al_2O_3$ molar ratio of 300, and the second reactor had a reaction temperature of 550° C., a reaction pressure of −0.42 MPa, and a WHSV of 5 $hr^{-1}$. The feedstock used herein was the mixture of methanol and dimethyl ether in a weight ratio of 1:1, and the weight ratio of water steam to the total amount of methanol and dimethyl ether is 3. The water in the needed amount was first mixed with the feedstock and then the mixture was subject to vaporization prior to enter into the reactor. The product was analyzed by sampling after reacting for 2 hr. The reaction results were as follows: the yield of propylene was 39.32%, the yield of ethylene was 9.57%, and the conversion of methanol was 100%.

Example 4

The various steps and conditions in this example were the same as those in Example 1, except that: the molecular sieve in the first reactor was ZSM-5 molecular sieve catalyst having a $SiO_2/Al_2O_3$ molar ratio of 250, the first reactor had a reaction temperature of 500° C., a WHSV of 0.5 $hr^{-1}$ and a reaction pressure of −0.02 MPa; the molecular sieve in the second reactor was ZSM-5 molecular sieve catalyst having a $SiO_2/Al_2O_3$ molar ratio of 900, and the second reactor had a reaction temperature of 580° C., a reaction pressure of −0.01 MPa, and a WHSV of 45 $hr^{-1}$. The feedstock used herein was the mixture of methanol and dimethyl ether in a weight ratio of 1:3, and the weight ratio of water steam to the total amount of methanol and dimethyl ether is 0.2. The water in the needed amount was first mixed with the feedstock and then the mixture was subject to vaporization prior to enter into the reactor. The product was analyzed by sampling after reacting for 2 hr. The reaction results were as follows: the yield of propylene was 33.32%, the yield of ethylene was 6.18%, and the conversion of methanol was 99.6%.

Example 5

The various steps and conditions in this example were the same as those in Example 1, except that: the molecular sieve in the first reactor was ZSM-5 molecular sieve catalyst having a $SiO_2/Al_2O_3$ molar ratio of 300, the first reactor had a reaction temperature of 400° C., a WHSV of 6 $hr^{-1}$ and a reaction pressure of 0.2 MPa; the molecular sieve in the second reactor was ZSM-5 molecular sieve catalyst having a $SiO_2/Al_2O_3$ molar ratio of 180, and the second reactor had a reaction temperature of 550° C., a reaction pressure of 0 MPa, and a WHSV of 2 $hr^{-1}$. The feedstock used herein was the pure dimethyl ether, and the weight ratio of water steam to dimethyl ether is 1:1. The water in the needed amount was first mixed with dimethyl ether and then the mixture was subject to vaporization prior to enter into the reactor. The product was analyzed by sampling after reacting for 2 hr. The reaction results were as follows: the yield of propylene was 46.32%, the yield of ethylene was 11.67%, and the conversion of methanol was 100%.

Example 6

The various steps and conditions in this example were the same as those in Example 1, except that: the molecular sieve in the first reactor was ZSM-11 molecular sieve catalyst having a $SiO_2/Al_2O_3$ molar ratio of 150, the first reactor had a reaction temperature of 380° C., a WHSV of 8 $hr^{-1}$ and a reaction pressure of 0.02 MPa; the molecular sieve in the second reactor was ZSM-11 molecular sieve catalyst having a SiO$_2$/Al$_2$O$_3$ molar ratio of 500, and the second reactor had a reaction temperature of 500° C., a reaction pressure of 0.03 MPa, and a WHSV of 3.6 hr$^{-1}$. The feedstock used herein was the pure methanol, and the weight ratio of water steam to methanol is 1:0.5. The water in the needed amount was first mixed with methanol and then the mixture was subject to vaporization prior to enter into the reactor. The product was analyzed by sampling after reacting for 2 hr. The reaction results were as follows: the yield of propylene was 32.17%, and the yield of ethylene was 5.64%.

Example 7

The various steps and conditions in this example were the same as those in Example 1, except that: the molecular sieve in the first reactor was ZSM-5 molecular sieve catalyst having a SiO$_2$/Al$_2$O$_3$ molar ratio of 120, the first reactor had a reaction temperature of 210° C., a WHSV of 30 hr$^{-1}$ and a reaction pressure of 1 MPa; the molecular sieve in the second reactor was ZSM-5 molecular sieve catalyst having a SiO$_2$/Al$_2$O$_3$ molar ratio of 260, and the second reactor had a reaction temperature of 510° C., a reaction pressure of −0.071 MPa, and a WHSV of 27 hr$^{-1}$. The feedstock used herein was the pure methanol, and the weight ratio of water steam to methanol is 1:3. The water in the needed amount was first mixed with methanol and then the mixture was subject to vaporization prior to enter into the reactor. The product was analyzed by sampling after reacting for 2 hr. The reaction results were as follows: the yield of propylene was 40.93%, and the yield of ethylene was 9.24%.

Example 8

The various steps and conditions in this example were the same as those in Example 7, except that: the molecular sieve in the first reactor was Y zeolite catalyst having a SiO$_2$/Al$_2$O$_3$ molar ratio of 10, the first reactor had a reaction temperature of 270° C., a WHSV of 7 hr$^{-1}$ and a reaction pressure of 1 MPa; the molecular sieve in the second reactor was ZSM-5 molecular sieve catalyst having a SiO$_2$/Al$_2$O$_3$ molar ratio of 260, and the second reactor had a reaction temperature of 510° C., a reaction pressure of 0.08 MPa, and a WHSV of 3 hr$^{-1}$. The feedstock used herein was the pure methanol, and the weight ratio of water steam to methanol is 1:3. The water in the needed amount was first mixed with methanol and then the mixture was subject to vaporization prior to enter into the reactor. The product was analyzed by sampling after reacting for 2 hr. The reaction results were as follows: the yield of propylene was 43.26%, and the yield of ethylene was 10.78%.

Example 9

The various steps and conditions in this example were the same as those in Example 8, except that: the molecular sieve in the first reactor was beta zeolite catalyst having a SiO$_2$/Al$_2$O$_3$ molar ratio of 50, the first reactor had a reaction temperature of 190° C., a WHSV of 15 hr$^{-1}$ and a reaction pressure of 1.0 MPa; the molecular sieve in the second reactor was ZSM-5 molecular sieve catalyst having a SiO$_2$/Al$_2$O$_3$ molar ratio of 80, and the second reactor had a reaction temperature of 480° C., a reaction pressure of −0.059 MPa, and a WHSV of 3.2 hr$^{-1}$. The feedstock used herein was the pure methanol, and the weight ratio of water steam to methanol is 1:4. The water in the needed amount was first mixed with methanol and then the mixture was subject to vaporization prior to enter into the reactor. The product was analyzed by sampling after reacting for 2 hr. The reaction results were as follows: the yield of propylene was 40.25%, and the yield of ethylene was 6.15%.

Example 10

The various steps and conditions in this example were the same as those in Example 9, except that: the molecular sieve in the first reactor was mordenite catalyst having a SiO$_2$/Al$_2$O$_3$ molar ratio of 120, the first reactor had a reaction temperature of 350° C., a WHSV of 0.6 hr$^{-1}$ and a reaction pressure of 0.8 MPa; the molecular sieve in the second reactor was ZSM-5 molecular sieve catalyst having a SiO$_2$/Al$_2$O$_3$ molar ratio of 170, and the second reactor had a reaction temperature of 485° C., a reaction pressure of 0.04 MPa, and a WHSV of 5 hr$^{-1}$. The feedstock used herein was the pure dimethyl ether, and the weight ratio of water steam to dimethyl ether is 1:10. The water in the needed amount was first mixed with methanol and then the mixture was subject to vaporization prior to enter into the reactor. The product was analyzed by sampling after reacting for 2 hr. The reaction results were as follows: the yield of propylene was 30.78%, and the yield of ethylene was 5.48%.

Example 11

The various steps and conditions in this example were the same as those in Example 5, except that: the reactor included a first rector, a second reactor and a third reactor connected in series; the catalyst used in any of the reactors was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of −0.053 MPa; the second reactor had a reaction temperature of 450° C., a WHSV of 50 hr$^{-1}$ and a reaction pressure of 0 MPa; and the third reactor had a reaction temperature of 490° C., a WHSV of 2 hr$^{-1}$ and a reaction pressure of 0 MPa. The feedstock used herein was the pure methanol, and the weight ratio of water steam to methanol is 0.4:1. The water in the needed amount was first mixed with methanol and then the mixture was subject to vaporization prior to enter into the reactor. The product was analyzed by sampling after reacting for 2 hr. The reaction results were as follows: the yield of ethylene was 10.02%, and the yield of propylene was 46.87%.

Example 12

The various steps and conditions in this example were the same as those in Example 11, except that: a fourth reactor was connected in series behind the third reactor; the catalyst used in any of the reactors was ZSM-5 molecular sieve catalyst having a SiO$_2$/Al$_2$O$_3$ molar ratio of 300; the first reactor had a reaction temperature of 410° C., a WHSV of 70 hr$^{-1}$ and a reaction pressure of −0.053 MPa; the second reactor had a reaction temperature of 480° C., a WHSV of 50 hr$^{-1}$ and a reaction pressure of 0 MPa; the third reactor had a reaction temperature of 460° C., a WHSV of 48 hr$^{-1}$ and a reaction pressure of 0 MPa; and the fourth reactor had a reaction temperature of 500° C., a WHSV of 2 hr$^{-1}$ and a reaction pressure of 0 MPa. The feedstock used herein was the pure methanol, and the weight ratio of water steam to methanol is 0.4:1. The water in the needed amount was first mixed with methanol and then the mixture was subject to vaporization prior to enter into the reactor. The product was analyzed by sampling after reacting for 2 hr. The reaction results were as follows: the yield of ethylene was 10.52%, the yield of propylene was 47.01%, and the conversion of methanol is 100%.

Example 13

The various steps and conditions in this example were the same as those in Example 12, except that: a fifth reactor was connected in series behind the fourth reactor; the catalyst used in any of the reactors was ZSM-5 molecular sieve catalyst having a $SiO_2/Al_2O_3$ molar ratio of 300; the first reactor had a reaction temperature of 410° C., a WHSV of 70 hr$^{-1}$ and a reaction pressure of −0.053 MPa; the second reactor had a reaction temperature of 480° C., a WHSV of 50 hr$^{-1}$ and a reaction pressure of 0 MPa; the third reactor had a reaction temperature of 500° C., a WHSV of 48 hr$^{-1}$ and a reaction pressure of 0 MPa; the fourth reactor had a reaction temperature of 480° C., a WHSV of 30 hr$^{-1}$ and a reaction pressure of 0 MPa; and the fifth reactor had a reaction temperature of 530° C., a WHSV of 2 hr$^{-1}$ and a reaction pressure of 0 MPa. The feedstock used herein was the pure methanol, and the weight ratio of water steam to methanol is 0.4:1. The water in the needed amount was first mixed with methanol and then the mixture was subject to vaporization prior to enter into the reactor. The product was analyzed by sampling after reacting for 2 hr. The reaction results were as follows: the yield of ethylene was 12.41%, the yield of propylene was 47.36%, and the conversion of methanol is 100%.

Example 14

The catalyst used in the example was ZSM-5 type molecular sieve catalyst made according to the various steps described in Example 1. The catalyst was activated at 480° C. in a $N_2$ atmosphere for 2 hr prior to reaction. The catalyst used in both the first and the second reactors was the above ZSM-5 molecular sieve catalyst. The first reactor used ZSM-5 molecular sieve having a $SiO_2/Al_2O_3$ molar ratio of 50, and had a reaction temperature of 450° C., a WHSV of 12 hr$^{-1}$, and the reaction pressure of 0.02 MPa; the second reactor used ZSM-5 molecular sieve having a $SiO_2/Al_2O_3$ molar ratio of 300, and had a reaction temperature of 500° C., the reaction pressure of 0.02 MPa, and a WHSV of 3.2 hr$^{-1}$. The feedstock used herein was the pure methanol, and the weight ratio of water steam to methanol is 1:2. The water in the needed amount was first mixed with methanol and then the mixture was subject to vaporization prior to enter into the reactor. The experimental results of the life of the catalyst were listed in Table 1.

TABLE 1

Experiments on life of the catalyst

| | Reaction time, hr | | | | | | | |
|---|---|---|---|---|---|---|---|---|
| | 5 | 50 | 120 | 200 | 320 | 400 | 420 | 540 |
| Yield of ethylene□% | 9.21 | 9.40 | 9.30 | 9.18 | 9.08 | 9.03 | 8.97 | 8.95 |
| Yield of Propylene□% | 40.81 | 40.95 | 40.15 | 41.03 | 39.87 | 39.26 | 39.25 | 39.12 |

Example 15

The catalyst used in the example was ZSM-5 type molecular sieve catalyst made according to the various steps described in Example 1. The catalyst was activated at 480° C. in a $N_2$ atmosphere for 2 hr prior to reaction. The catalyst used in both the first and the second reactors was the above ZSM-5 molecular sieve catalyst. The first reactor used ZSM-5 molecular sieve having a $SiO_2/Al_2O_3$ molar ratio of 60, and had a reaction temperature of 450° C., a WHSV of 10 hr$^{-1}$, and the reaction pressure of normal pressure; the second reactor used ZSM-5 molecular sieve having a $SiO_2/Al_2O_3$ molar ratio of 280, and had a reaction temperature of 500° C., the reaction pressure of normal pressure, and a WHSV of 4.0 hr$^{-1}$. The feedstock used herein was the pure methanol, and the weight ratio of ethanol as the diluting agent to methanol is 0.2:1. The ethanol in the needed amount was first mixed with methanol and then the mixture was subject to vaporization prior to enter into the reactor. The reaction results were as follows: the yield of ethylene was 16.3%, and the yield of propylene was 43.5%.

Comparative Example 1

The various steps and conditions were the same as those described in Example 14 except that: a single reactor was used, the ZSM-5 molecular sieve had a $SiO_2/Al_2O_3$ molar ratio of 300, the reaction temperature was 500° C., the reaction pressure was 0.02 MPa, and a WHSV was 3.2 hr$^{-1}$. The feedstock used herein was the pure methanol, and the weight ratio of water steam to methanol is 1:2. The water in the needed amount was first mixed with methanol and then the mixture was subject to vaporization prior to enter into the reactor. The experimental results of the life of the catalyst were listed in Table 2.

TABLE 2

Experiments on life of the catalyst

| | Reaction time, hr | | | | | |
|---|---|---|---|---|---|---|
| | 5 | 50 | 127 | 203 | 325 | 400 |
| Yield of ethylene□% | 9.17 | 9.08 | 9.01 | 8.76 | 8.31 | 7.98 |
| Yield of Propylene□% | 41.36 | 41.71 | 40.83 | 38.08 | 36.63 | 32.26 |

Obviously, the technical solution of the present invention could markedly prolong the active period of the catalyst, which had obvious technical advantage.

The invention claimed is:

1. A process for producing lower olefins herein, which is carried out under the conditions of catalytic cracking methanol and dimethyl ether and the presence of diluting gas, and adopts as a feedstock methanol, dimethyl ether or their mixture, comprises the steps of:
   a) introducing the feedstock firstly enter a first reaction zone to contact with a first crystalline aluminosilicate catalyst having a $SiO_2/Al_2O_3$ molar ratio of at least 10, to thereby produce a first reaction effluent containing lower olefins;
   b) introducing the first reaction effluent enter in turn at least one second reaction zone to contact with a second crystalline aluminosilicate catalyst having a $SiO_2/Al_2O_3$ molar ratio of at least 10, to thereby produce a second reaction effluent containing lower olefins; and
   c) separating lower olefins from the second reaction effluent;
   wherein, the weight ratio of the diluting gas to the feedstock is 0.01-6:1, the reaction pressure in the first reaction zone is−0.1-1 MPa, and the reaction pressure in the second reaction zone is −0.09-0.5 MPa, and the reaction temperature in the first reaction zone is lower by 30 to 150° C. than that in the second reaction zone, and the WHSV of the first reaction zone is higher by 3-20 hr$^{-1}$ than that of the second reaction zone.

2. The process as claimed in claim 1, wherein the diluting agent is selected from water, steam, ethanol, and mixture thereof.

3. The process as claimed in claim 2, wherein the weight ratio of the diluting agent to the feedstock is 0.2-3:1.

4. The process as claimed in claim 1, wherein the first reaction zone has a WHSV of 0.1-70 hr$^{-1}$; and at least one second reaction zone has a WHSV of 0.1-50 hr$^{-1}$.

5. The process as claimed in claim 4, wherein the first reaction zone has a reaction temperature of 300-480° C., a WHSV of 1-50 hr$^{-1}$, and a reaction pressure of –0.04-0.5 MPa; and at least one second reaction zone has a reaction temperature of 450-550° C., a WHSV of 1-20 hr$^{-1}$, and a reaction pressure of –0.04-0.5 MPa.

6. The process as claimed in claim 1, wherein the reaction pressure in both the first and second reaction zones is –0.1-<0 MPa.

7. The process as claimed in claim 1, wherein the first crystalline aluminosilicates are solid acid molecular sieve catalyst having a $SiO_2/Al_2O_3$ molar ratio of 10-1,000, and the second crystalline aluminosilicates are solid acid molecular sieve catalyst having a $SiO_2/Al_2O_3$ molar ratio of 80-800.

8. The process as claimed in claim 1, wherein both the first and second crystalline aluminosilicates are selected from ZSM-5 molecular sieves having a $SiO_2/Al_2O_3$ molar ratio of 100-700.

9. The process as claimed in claim 1, wherein at least one of the second reaction zones includes 1-5 reactors in series.

10. The process as claimed in claim 9, wherein at least one of the second reaction zones includes 1-3 fixed-bed reactors in series.

11. The process as claimed in claim 1, wherein reactors for said catalytic cracking methanol and dimethyl ether are selected from axial fixed-bed reactors, radial fixed-bed reactors, and moving bed reactors.

12. The process as claimed in claim 2, wherein the diluting agent is ethanol.

13. The process as claimed in claim 1, wherein the reaction temperature in the first reaction zone is 190-500° C. and the reaction temperature in the second reaction zone is 400-580° C.

* * * * *